(12) United States Patent
Yano et al.

(10) Patent No.: US 7,425,401 B2
(45) Date of Patent: *Sep. 16, 2008

(54) CYANINE COMPOUNDS, OPTICAL RECORDING MATERIALS AND OPTICAL RECORDING MEDIA

(75) Inventors: Toru Yano, Tokyo (JP); Koichi Shigeno, Tokyo (JP); Mitsuhiro Okada, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/566,258

(22) PCT Filed: Jul. 27, 2004

(86) PCT No.: PCT/JP2004/010648

§ 371 (c)(1), (2), (4) Date: Jan. 30, 2006

(87) PCT Pub. No.: WO2005/014722

PCT Pub. Date: Feb. 17, 2005

(65) Prior Publication Data

US 2006/0286483 A1    Dec. 21, 2006

(30) Foreign Application Priority Data

Aug. 7, 2003  (JP) .............................. 2003-289166

(51) Int. Cl.
*G11B 7/24* (2006.01)
(52) U.S. Cl. ................. 430/270.21; 430/945; 428/64.4; 428/64.8; 369/284
(58) Field of Classification Search ........................ None
See application file for complete search history.

(56) References Cited

U.S. PATENT DOCUMENTS

| | | | | |
|---|---|---|---|---|
| 4,735,839 | A | * | 4/1988 | Sato et al. .................. 428/64.7 |
| 6,821,708 | B2 | * | 11/2004 | Liao et al. ............... 430/270.19 |
| 7,316,836 | B2 | * | 1/2008 | Wada et al. ................ 428/64.1 |
| 2005/0031993 | A1 | * | 2/2005 | Yano et al. ............. 430/270.21 |
| 2005/0094548 | A1 | * | 5/2005 | Wada et al. ............... 369/275.4 |
| 2006/0110566 | A1 | * | 5/2006 | Wada et al. ................ 428/64.1 |
| 2007/0259294 | A1 | * | 11/2007 | Shigeno et al. .......... 430/495.1 |
| 2008/0033179 | A1 | * | 2/2008 | Yano et al. ............... 546/277.4 |

FOREIGN PATENT DOCUMENTS

| | | |
|---|---|---|
| JP | 58-21746 | 2/1983 |
| JP | 03-224793 | * 10/1991 |
| JP | 10-278426 | 10/1998 |
| JP | 11-227331 | 8/1999 |
| JP | 11-227904 | 10/1999 |
| JP | 2000-108510 | * 4/2000 |
| JP | 2000-168233 | * 6/2000 |
| JP | 2000-289335 | * 10/2000 |
| JP | 2002-052829 | 2/2002 |
| JP | 2003-231359 | 8/2003 |
| JP | 2003-335061 | 11/2003 |

OTHER PUBLICATIONS

JPO abstract of JP 03-224793 (1991).*
Machine Translation of JP 10-278426.*
Machine Translation of JP 2003-335061.*
Machine Translation of JP 2003-231359.*

* cited by examiner

*Primary Examiner*—Martin J Angebrannt
(74) *Attorney, Agent, or Firm*—Young & Thompson

(57) ABSTRACT

An optical recording medium containing a cyanine dyes of formula:

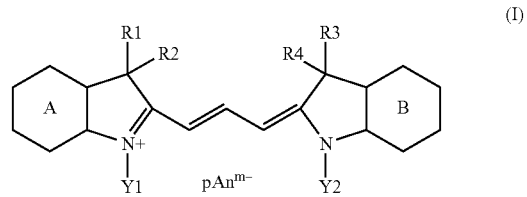

Where at least one pair of R1 & R2 and R3 & R4 are benzyl moieties, rings A and B are each a benzene or naphthalene ring, Y1 and Y2 are C 1-30 organic groups and $An^{m-}$ is an m valent anion, present in an integer p.

2 Claims, 8 Drawing Sheets

Fig. 1-a
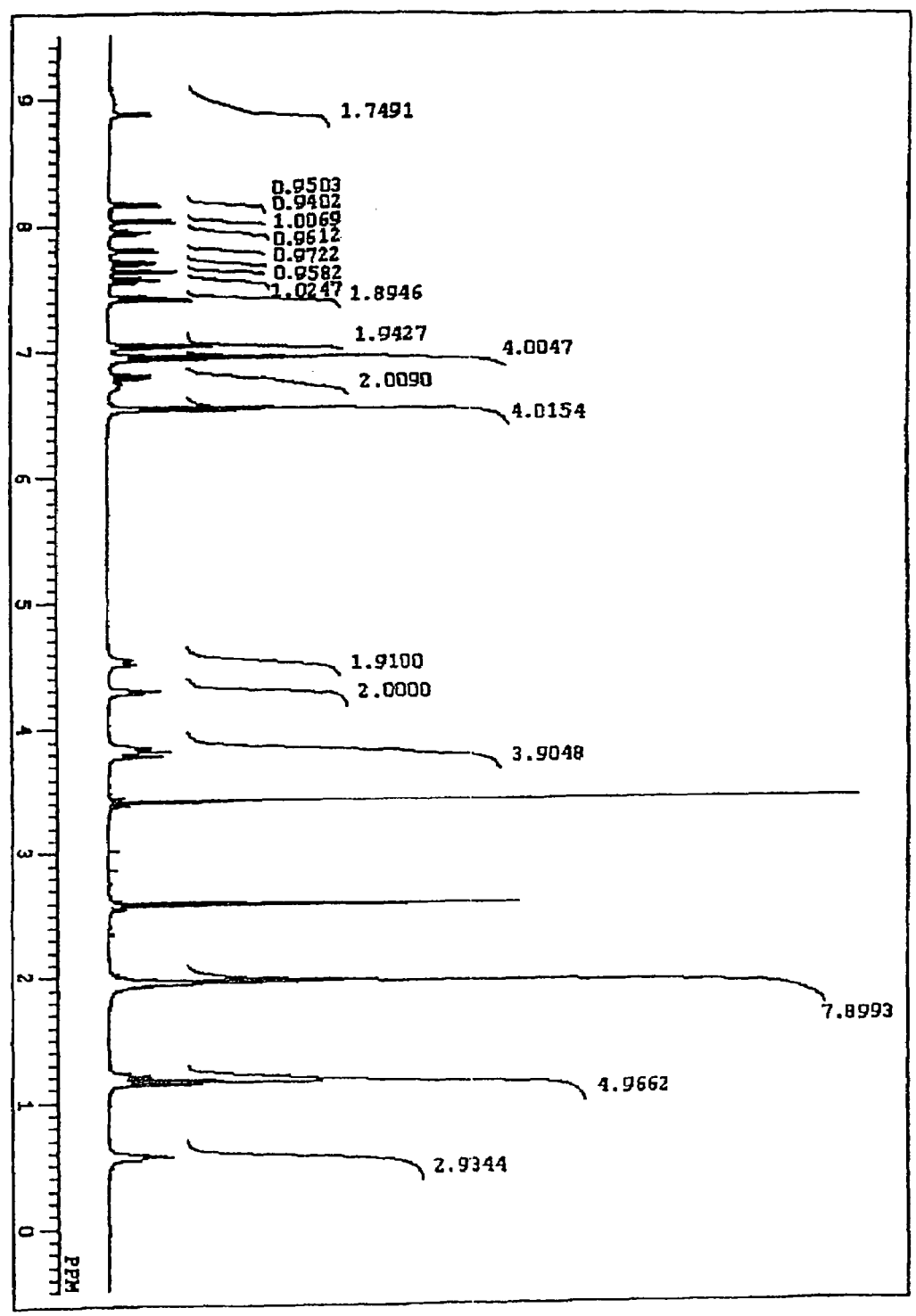

Fig. 1-b
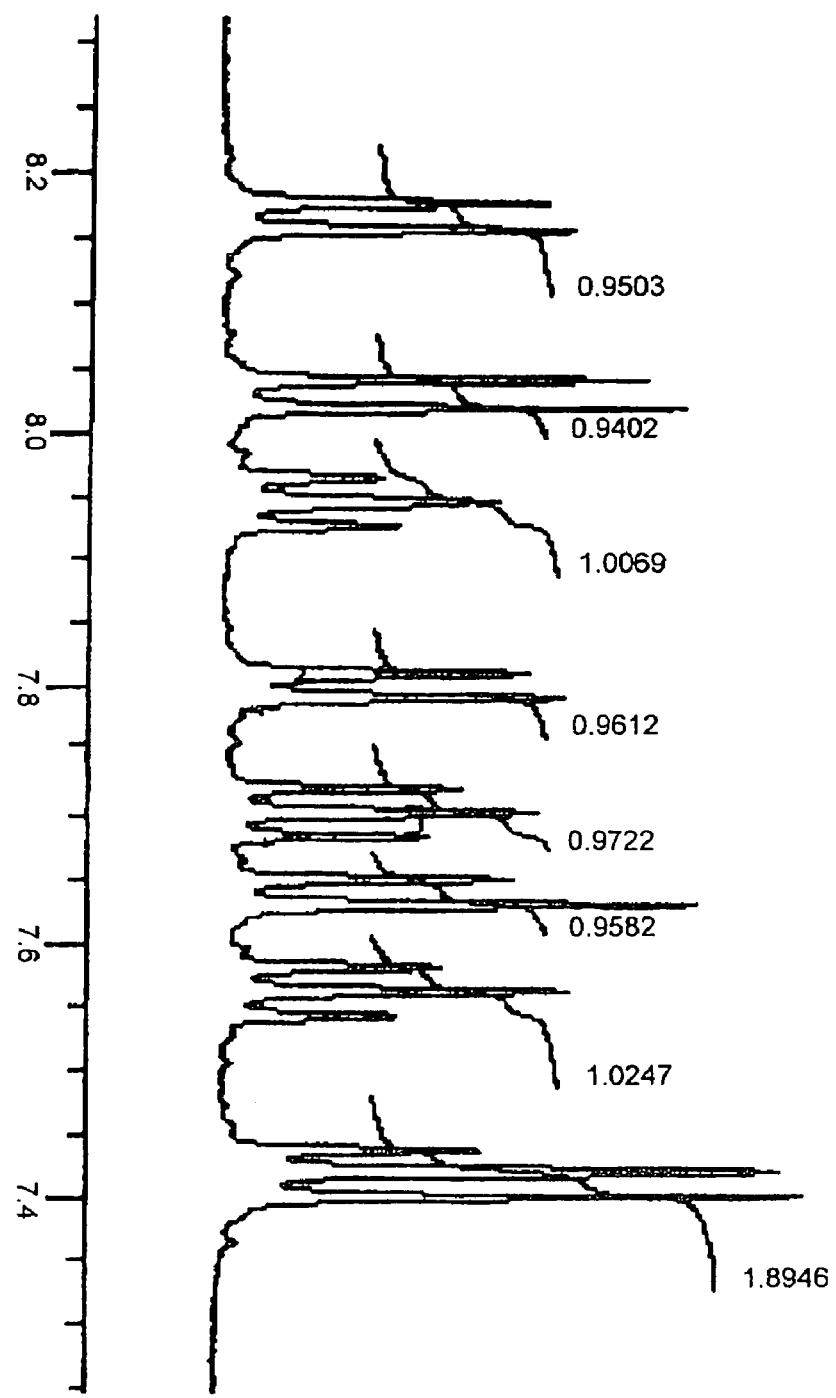

Fig. 2-a
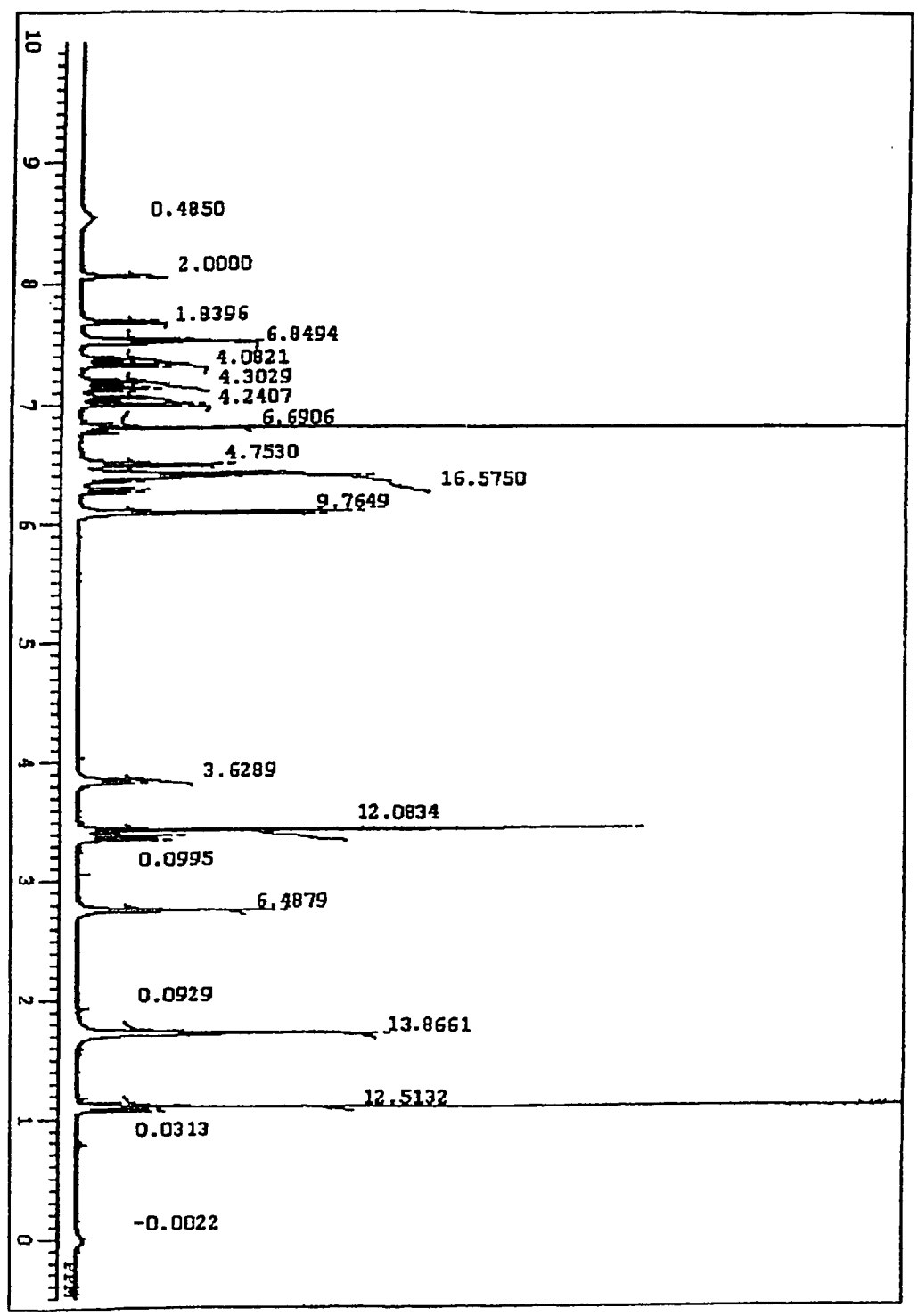

Fig. 2-b
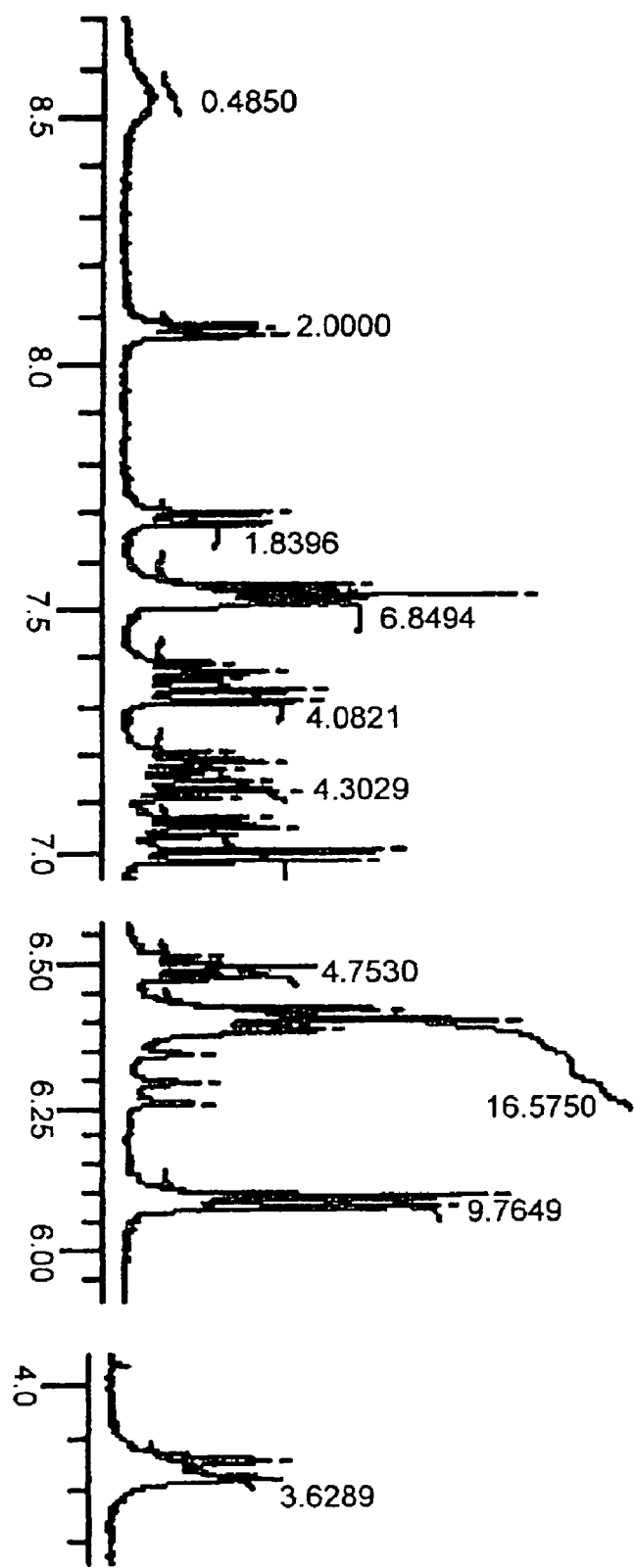

Fig. 2-c
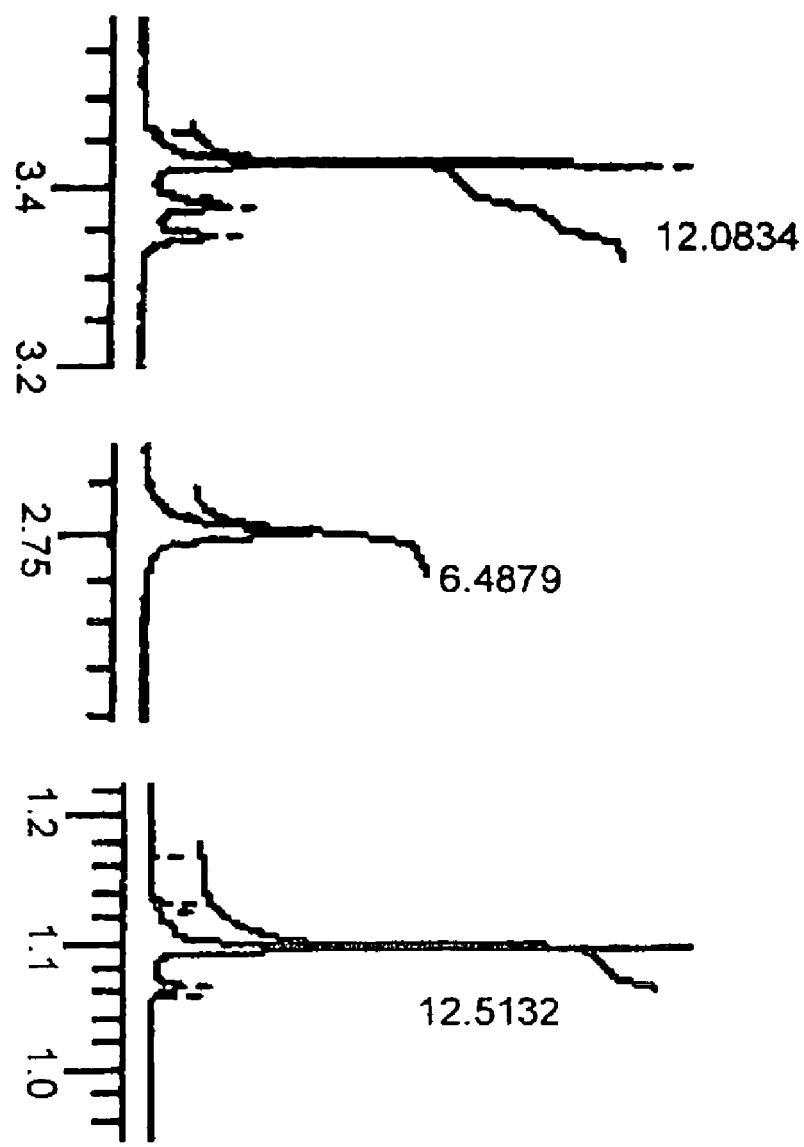

Fig. 3-a
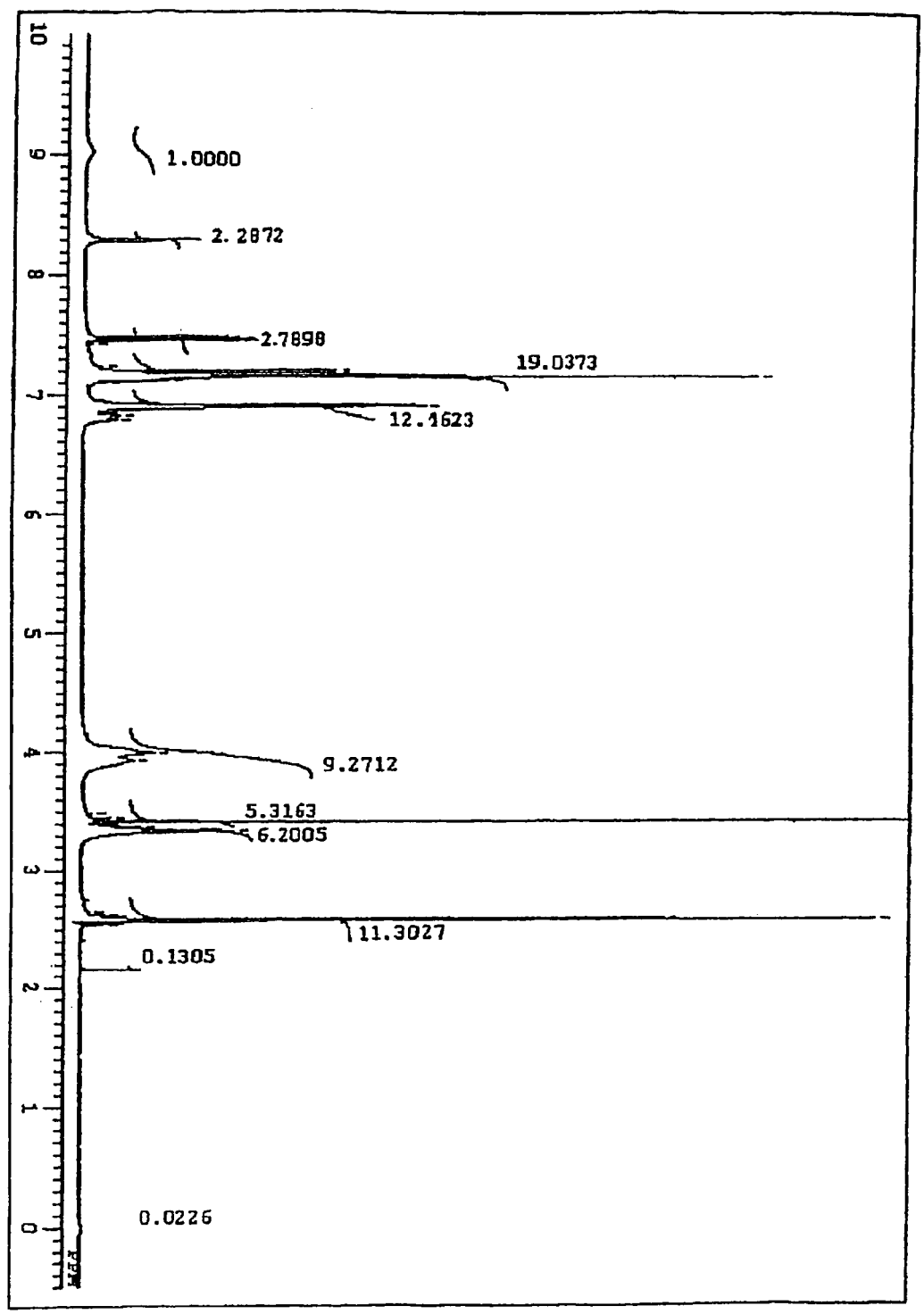

Fig. 3-b
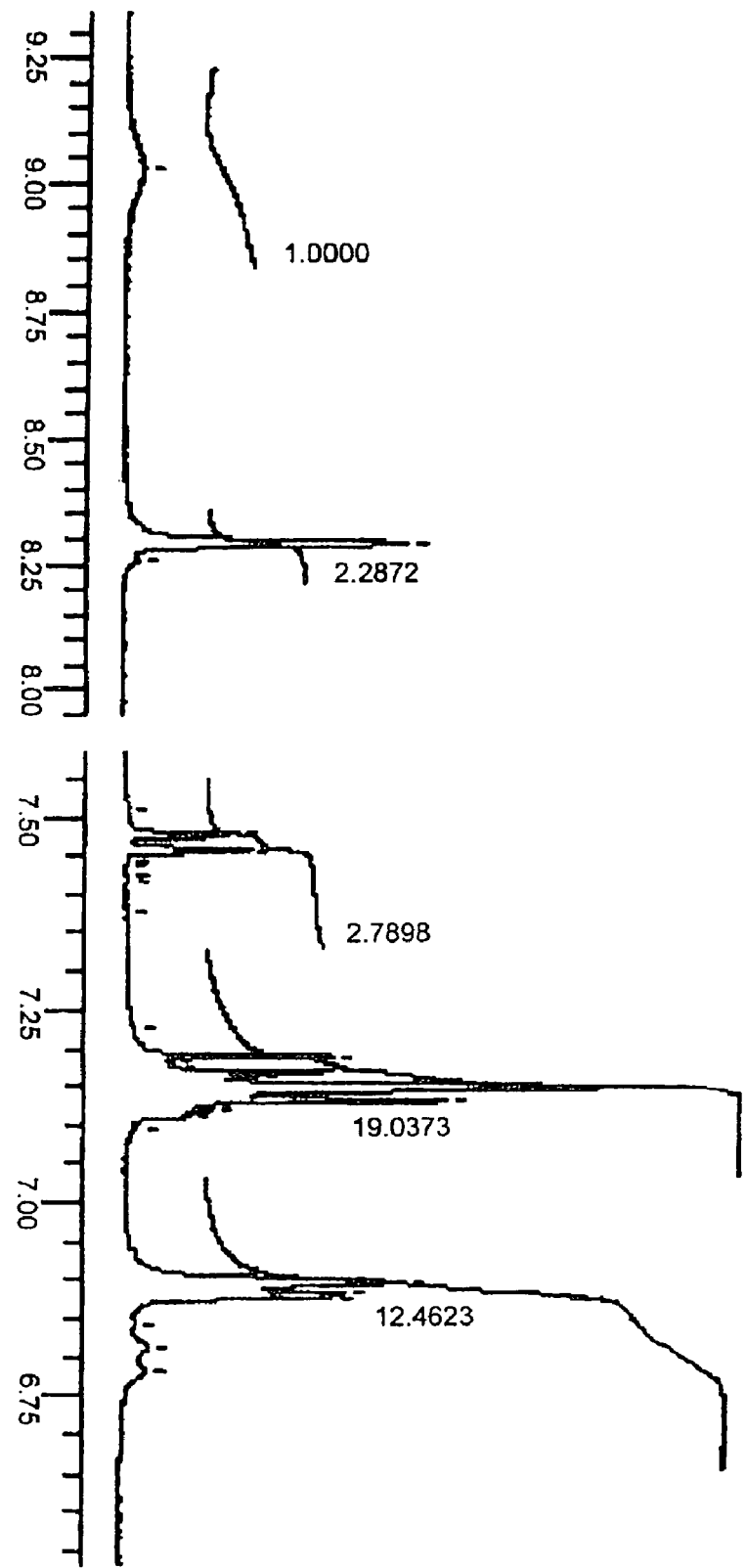

Fig. 3-c
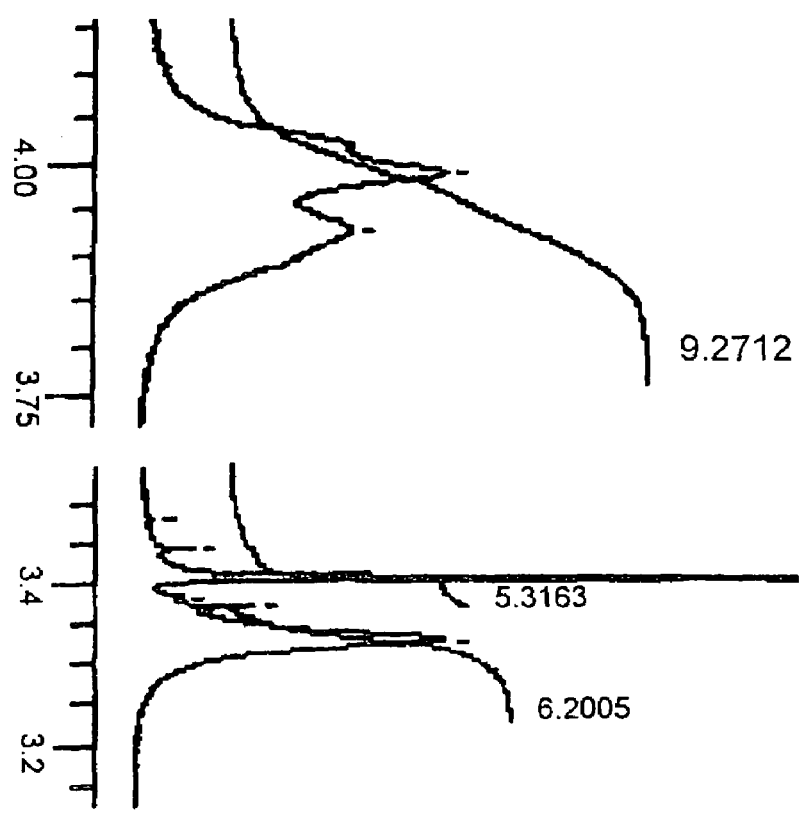

CYANINE COMPOUNDS, OPTICAL RECORDING MATERIALS AND OPTICAL RECORDING MEDIA

TECHNICAL FIELD

This invention relates to a novel cyanine compound. More particularly, it relates to a cyanine compound having a specific structure suited for use in optical elements, especially an optical filter of image displays or a laser optical recording material.

BACKGROUND ART

Compounds having a large absorption in a range of 500 to 700 nm, particularly those having a maximum absorption ($\lambda_{max}$) in a range of 550 to 620 nm are used as optical elements including a recording layer of optical recording media, such as DVD-Rs, and an optical filter of image displays, such as liquid crystal displays (LCDs), plasma display panels (PDPs), electroluminescence displays (ELDs), cathode ray tube displays (CRTs), fluorescent tube displays, and field emission displays.

For applications to the optical elements, a number of cyanine compounds having an indole ring which have high sensitivity have been studied. There have been made many reports on this type of cyanine compounds particularly for their capability of coping with increasing recording speeds in applications as a recording element in optical recording media represented by DVD-Rs. Among them are Patent Document 1, Patent Document 2, Patent Document 3, and Patent Document 4 (hereinafter referred to as references-1 to 4). References-1 to 3 disclose cyanine compounds which may have an aralkyl group at the 3-position of the indole ring. While these compounds are analogous to the cyanine compound of the present invention, the references are silent on the method and effects of introducing an aralkyl group to the cyanine compound. Additionally, these and other known cyanine compounds are unsatisfactory in thermal decomposition characteristics. In optical recording material applications, compounds having low decomposition temperatures are suited. The cyanine compounds described in references-1 to 4 are not satisfactory in this aspect, nevertheless.

Patent Document 1: JP-A-10-278426
Patent Document 2: JP-A-11-227331
Patent Document 3: JP-A-11-277904
Patent Document 4: JP-A-2002-52829

DISCLOSURE OF THE INVENTION

Problems to be Solved by the Invention:

The problem to be solved, as stated above, is that no compound is available that shows thermal decomposition behavior suitable for high-speed recording applications and is therefore useful particularly as a recording element of an optical recording medium.

Accordingly, an object of the present invention is to provide a novel cyanine compound exhibiting thermal behavior suited to optical recording applications and an optical recording material and an optical recording medium containing the same.

The present inventors thought that thermal decomposition behavior control and absorption wavelength control would be effective in achieving a sensitivity sufficient to cope with the demand for high-speed recording. As a result of extensive investigations, they have found that a cyanine compound having a specific molecular structure meets the above object.

The present invention has been accomplished based on the above finding. The present invention provides a cyanine compound represented by general formula (I) shown below, an optical recording material containing the cyanine compound that is used to form an optical recording layer on a substrate to make an optical recording medium, and an optical recording medium having a thin film of the optical recording material formed on a substrate as an optical recording layer.

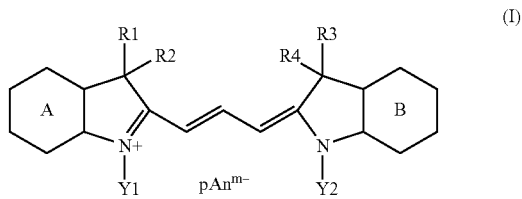

(I)

wherein ring A and ring B each represent a benzene or naphthalene ring that may be substituted; at least one of the pair of adjacent groups R1 and R2 and the pair of adjacent groups R3 and R4 represent a pair of benzyl groups, and the other paired groups each represent an alkyl group having 1 to 4 carbon atoms or are connected to each other to form a 3- to 6-membered ring; Y1 and Y2 each represent an organic group having 1 to 30 carbon atoms; $An^{m-}$ represents an m-valent anion; m represents an integer 1 or 2; and p represents a coefficient for maintaining the charge neutrality.

BRIEF DESCRIPTION OF THE DRAWINGS

FIG. 1-*a* shows the $^1$H-NMR spectrum of the hexafluorophosphate of compound No. 10 obtained in Preparation Example 1.
FIG. 1-*b* presents a fragmentary enlargement of FIG. 1-*a*.
FIG. 2-*a* shows the $^1$H-NMR spectrum of the hexafluorophosphate of compound No. 12 obtained in Preparation Example 2.
FIG. 2-*b* presents a fragmentary enlargement of FIG. 2-*a*.
FIG. 2-*c* presents a fragmentary enlargement of FIG. 2-*a*.
FIG. 3-*a* represents the $^1$H-NMR spectrum of the hexafluorophosphate of compound No. 19 obtained in Preparation Example 3.
FIG. 3-*b* presents a fragmentary enlargement of FIG. 3-*a*.
FIG. 3-*c* presents a fragmentary enlargement of FIG. 3-*a*.

BEST MODE FOR CARRYING OUT THE INVENTION

The cyanine compound of the invention represented by general formula (I) is a novel compound having benzyl groups at a specified position. It is characterized by a lower decomposition temperature than that of other cyanine compounds used in optical recording materials for DVD-R applications and by a proper absorption wavelength.

In general formula (I), the substituent of the benzene or naphthalene ring represented by ring A or B, which may be substituted, includes a halogen group such as fluorine, chlorine, bromine or iodine; an alkyl group such as methyl, ethyl, propyl, isopropyl, butyl, sec-butyl, tert-butyl, isobutyl, amyl, isoamyl, tert-amyl, hexyl, cyclohexyl, heptyl, isoheptyl, tert-heptyl, n-octyl, isooctyl, tert-octyl or 2-ethylhexyl; an aryl group such as phenyl, naphthyl, 2-methylphenyl, 3-methylphenyl, 4-methylphenyl, 4-vinylphenyl or 3-isopropylphenyl; an alkoxy group such as methoxy, ethoxy, propoxy, isopropoxy, butoxy, sec-butoxy or tert-butoxy, an alkylthio group such as methylthio, ethylthio, propylthio, isopropylthio, butylthio, sec-butylthio or tert-butylthio; a nitro group; and a cyano group.

The pair of R1 and R2 or the pair of R3 and R4 are a pair of benzyl groups, or each of R1, R2, R3, and R4 is a benzyl group. When the pair of R1 and R2 or the pair of R3 and R4 are other than a benzyl group, they each represent an alkyl group having 1 to 4 carbon atoms, or the pair of R1 and R2 or the pair of R3 and R4 are taken together to form a 3- to 6-membered ring. The alkyl group includes methyl, ethyl, propyl, isopropyl, butyl, sec-butyl, tert-butyl, and isobutyl. The 3- to 6-membered ring includes cyclopropane-1,1-diyl, cyclobutane-1,1-diyl, 2,4-dimethylcyclobutane-1,1-diyl, 3,3-dimethylcyclobutane-1,1-diyl, cyclopentane-1,1-diyl, cyclohexane-1,1-diyl, tetrahydropyran-4,4-diyl, thiane-4,4-diyl, piperidine-4,4-diyl, N-substituted piperidine-4,4-diyl, morpholine-2,2-diyl, morpholine-3,3-diyl, N-substituted morpholine-2,2-diyl, and N-substituted morpholine-3,3-diyl, in which the N-substituent includes the substituents that may be present on ring A.

The organic group having 1 to 30 carbon atoms as represented by Y1 or Y2 includes, but is not limited to, an alkyl group, e.g., methyl, ethyl, propyl, isopropyl, butyl, sec-butyl, tert-butyl, isobutyl, amyl, isoamyl t-amyl, hexyl, cyclohexyl, cyclohexylmethyl, 2-cyclohexylethyl, heptyl, isoheptyl, t-heptyl, n-octyl, isooctyl, t-octyl, 2-ethylhexyl, nonyl, isononyl, decyl, dodecyl, tridecyl, tetradecyl, pentadecyl, hexadeyl, heptadecyl or octadecyl; an alkenyl group, e.g., vinyl, 1-methylethenyl, 2-methylethenyl, propenyl, butenyl, isobutenyl, pentenyl, hexenyl, heptenyl, octenyl, decenyl, pentadecenyl or 1-phenylpropen-3-yl; phenyl, naphthyl,; an alkylaryl group, e.g., 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl or cyclohexylphenyl; and an arylalkyl group, e.g., benzyl, phenethyl, 2-phenylpropan-2-yl, diphenylmethyl, triphenylmethyl, styryl or cinnamyl. The organic group as Y1 and Y2 further includes the above-recited hydrocarbon groups which contain an ether linkage or a thioether linkage, such as 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 2-methylthioethyl, and 2-phenylthioethyl. These organic groups may be substituted with an alkoxy group, an alkenyl group, a nitro group, a cyano group, a halogen atom, etc.

A bulkier organic group as Y1 or Y2 reduces the molar absorptivity of the cyanine compound of the invention and can affect the sensitivity. From that viewpoint, the organic group is preferably selected from hydrocarbon groups having 1 to 8 carbon atoms, particularly alkyl groups having 1 to 8 carbon atoms.

Of the anions represented by $An^{m-}$ monovalent ones include halide anions, e.g., chloride, bromide, iodide and fluoride anions; inorganic anions, such as perchlorate, chlorate, thiocyanate, hexafluorophosphate, hexafluoroantimonate, and hexafluoroborate anions; organic sulfonate anions, such as benzenesulfonate, toluenesulfonate, trifluoromethanesulfonate, diphenylamine-4-sulfonate, 2-amino-5-methyl-5-chlorobenzenesulfonate, and 2-amino-5-nitrobenzenesulfonate anions; and organophosphate anions, such as octylphosphate, dodecylphosphate, octadecylphosphate, phenylphosphate, nonylphenylphosphate, and 2,2'-methylenebis(4,6-di-t-butylphenyl)phosphonate anions. Divalent ones include benzenedisulfonate and naphthalenedisulfonate anions. If desired, a quencher anion capable of deexciting (quenching) an active molecule in an excited state, a metallocene compound anion of, for example, a ferrocene or ruthenocene compound having an anionic group (e.g., carboxyl, phosphonic or sulfonic group) on the cyclopentadienyl ring, and the like can be used.

The quencher anion includes those represented by general formulae (A) or (B) shown below and those described in JP-A-60-234892, JP-A-5-43814, JP-A-6-239028, JP-A-9-309886, and JP-A-10-45767.

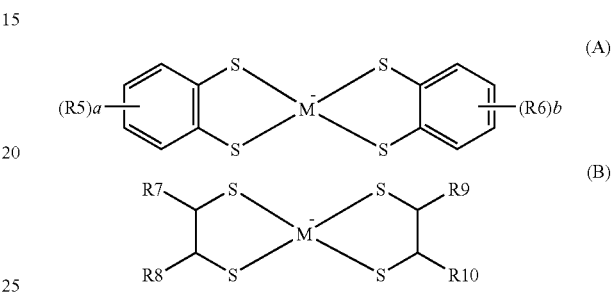

wherein M represents nickel or copper; R5 and R6 each represent a halogen atom, an alkyl group having 1 to 8 carbon atoms, an aryl group having 6 to 30 carbon atoms or —SO$_2$-Z; Z represents an alkyl group, an aryl group, a halogen-substituted aryl group, a dialkylamino group, a diarylamino group, a piperidino group or a morpholino group; a and b each represent an integer of 0 to 4; and R7, R8, R9, and R10 each represent an alkyl group, an alkylphenyl group, an alkoxyphenyl group or a halogen-substituted phenyl group.

Specific examples of the cyanine compound represented by general formula (I) according to the present invention are shown below. The formulae shown are cation moieties of the cyanine compounds.

Compound No. 1

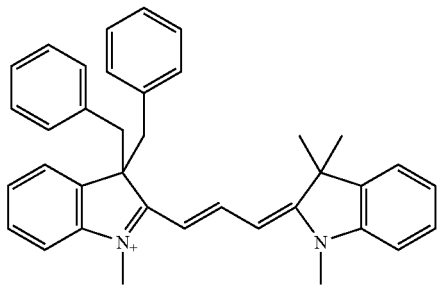

Compound No. 2

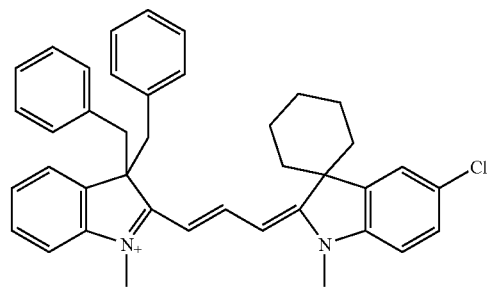

-continued
Compound No. 3
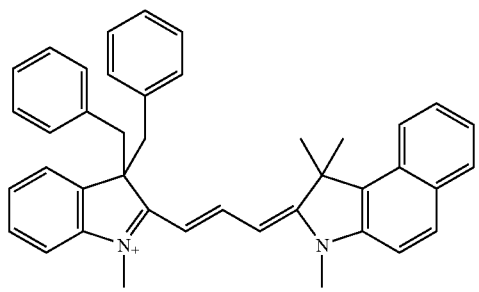
Compound No. 4
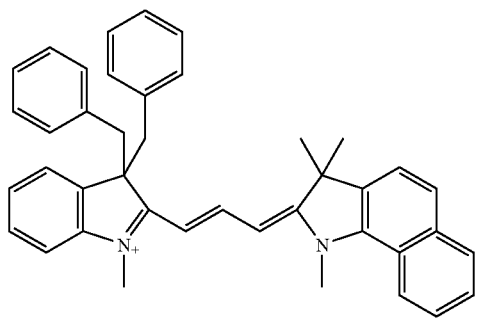
Compound No. 5
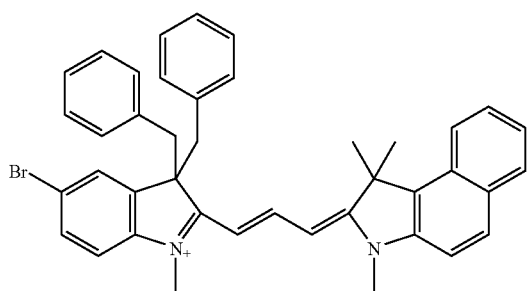
Compound No. 6
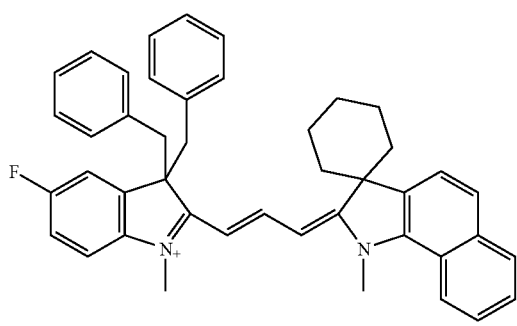
-continued
Compound No. 7
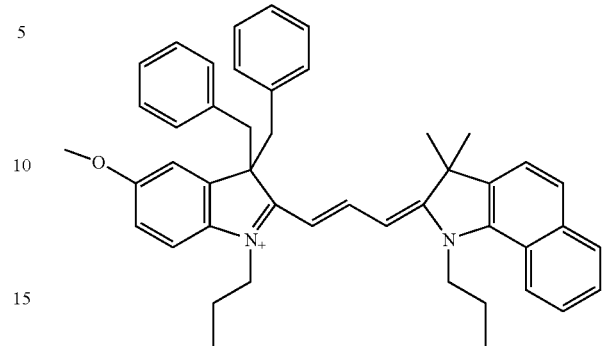
Compound No. 8
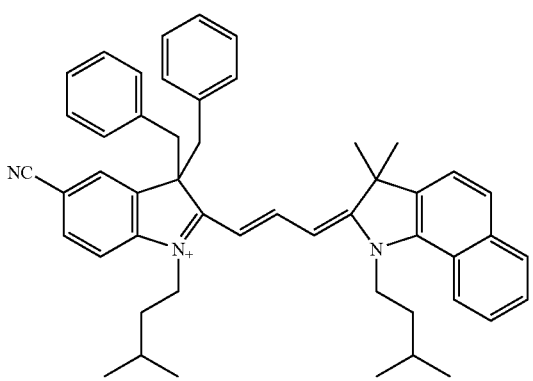
Compound No. 9
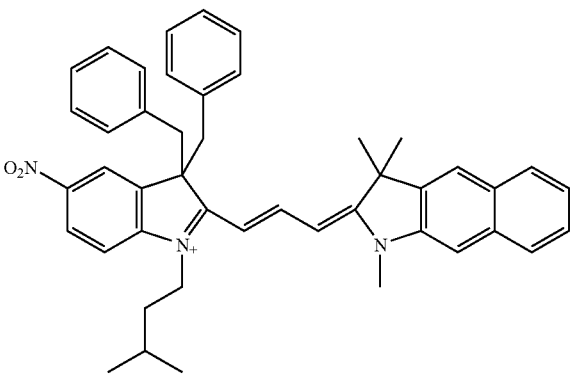
Compound No. 10
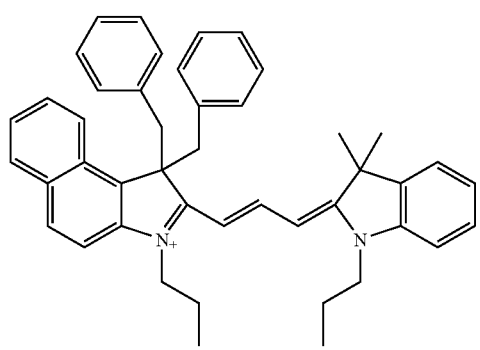

Compound No. 11
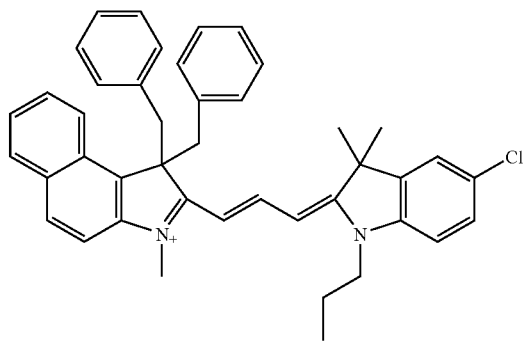
Compound No. 12
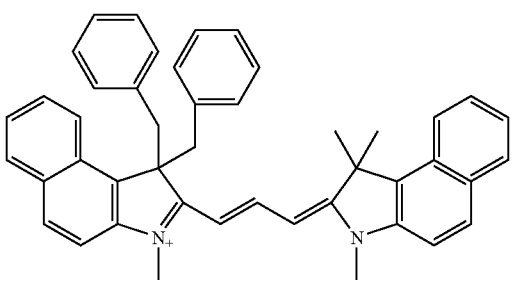
Compound No. 13
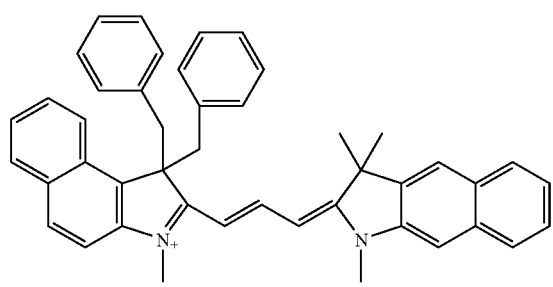
Compound No. 14
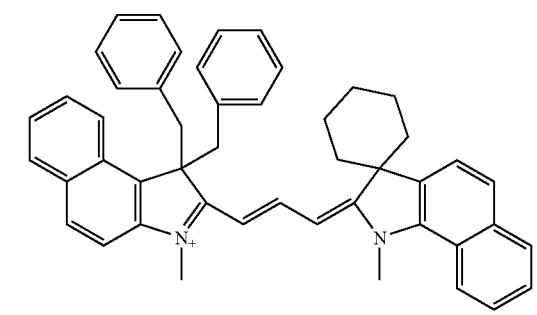
Compound No. 15
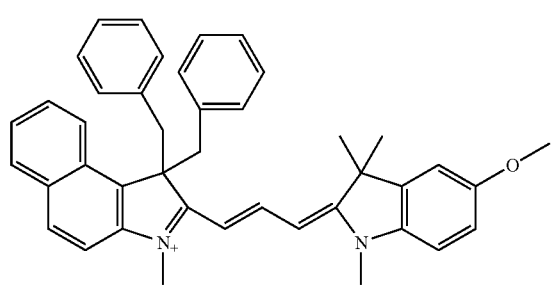
Compound No. 16
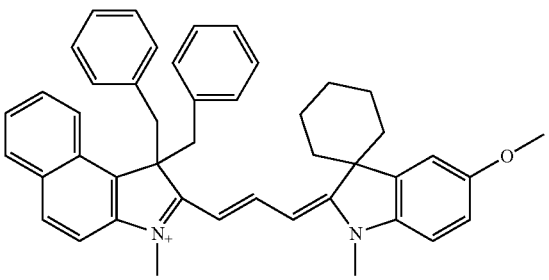
Compound No. 17
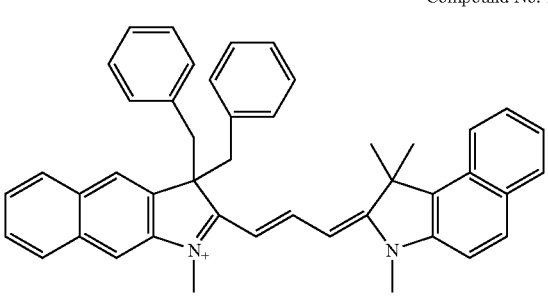
Compound no. 18
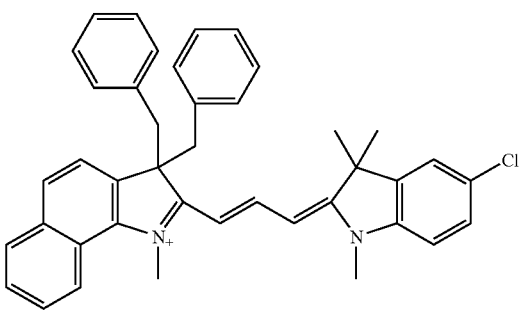
Compound No. 19
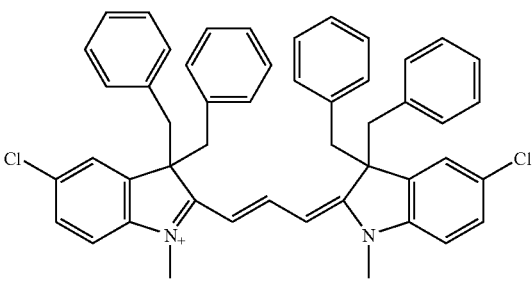
Compound No. 20
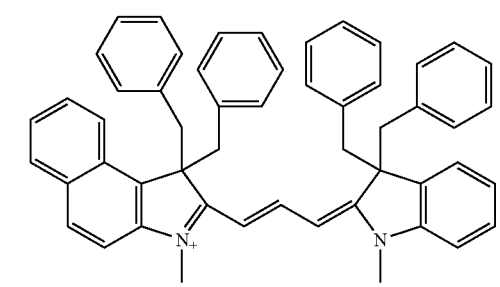

-continued

Compound No. 21

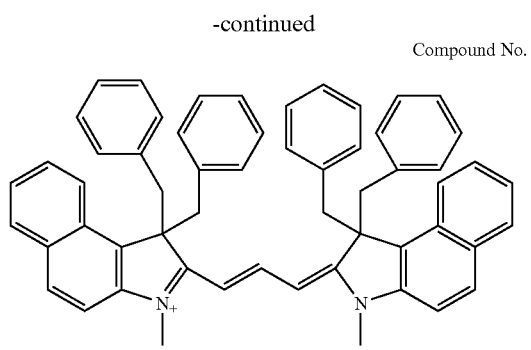

Compound No. 22

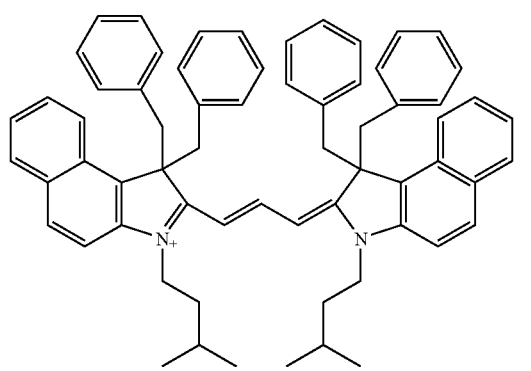

Compound No. 23

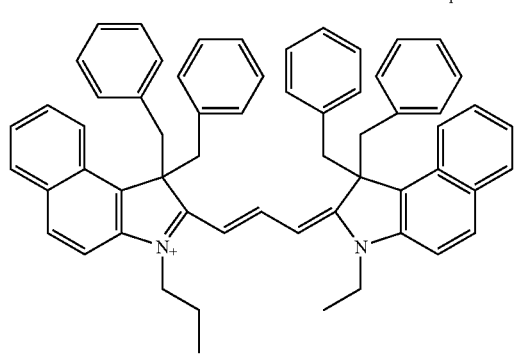

Compound No. 24

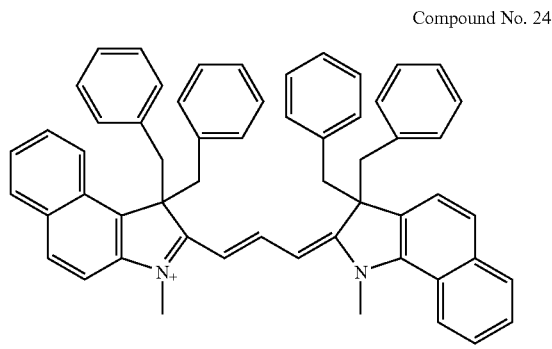

-continued

Compound No. 25

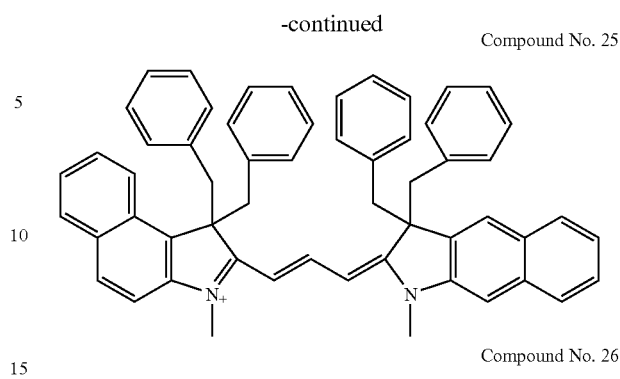

Compound No. 26

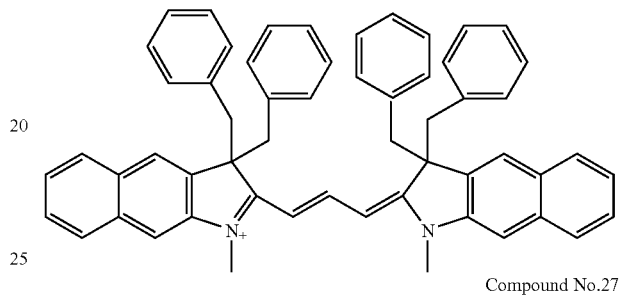

Compound No. 27

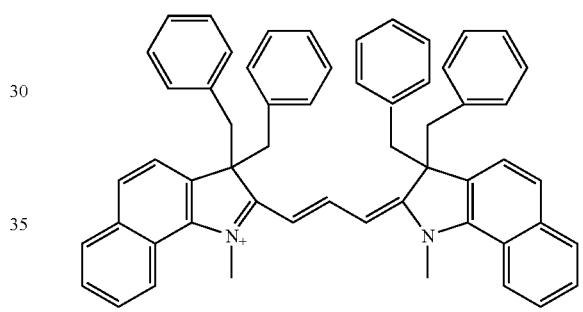

Of the above-described cyanine compounds preferred are those in which the ring constituting the indole skeleton having the two benzyl groups (i.e., ring A and/or ring B in general formula (I)) is a naphthalene ring (e.g., compound Nos. 10 to 18 and 20 to 27) because of their excellent thermal behavior for use as an optical recording material. Still preferred of them are those in which the benzene ring is fused to the e-face of the indole ring (e.g., compound Nos. 10 to 16 and 20 to 25). It is considered that the preferred compounds have their ring structure distorted increasingly due to the steric hindrance between the two benzyl groups and the benzoindole ring.

Also preferred are those in which each of R1, R2, R3, and R4 is a benzyl group, e.g., compound Nos. 19 to 27 because of their increased molecular distortion which can produce similar effects to those described above.

The cyanine compound represented by general formula (I) is not restricted by the process of preparation. The cyanine compound is obtained by, for example, linking two intermediate compounds, 2-methylindole quaternary salt derivatives, using a bridging agent, such as N,N'-diphenylamidine. The benzyl groups adjacent to each other can be introduced in the course of preparing the 2-methylindole quaternary salt derivative. For example, two benzyl groups can be introduced by forming an indole ring using an arylhydrazine derivative as a starting material and 1,1-dibenzylacetone. Alternatively, one benzyl group can be introduced by forming an indole ring using an arylhydrazine derivative as a starting material and 4-phenyl-2-butanone, and then another benzyl group is introduced by allowing the indole ring to react with a halogenated methylbenzene derivative. Y1 or Y2 can be introduced by using Y1-D or Y2-D (wherein D is a halogen group, e.g., chlorine, bromine or iodine, or a sulfonyloxy group, e.g., phenylsulfonyloxy, 4-methylphenylsulfonyloxy or 4-chlorophenylsulfonyloxy) reactive with NH of an arylamine derivative or an indole ring. A typical route for preparing the cyanine compound of the invention is shown below.

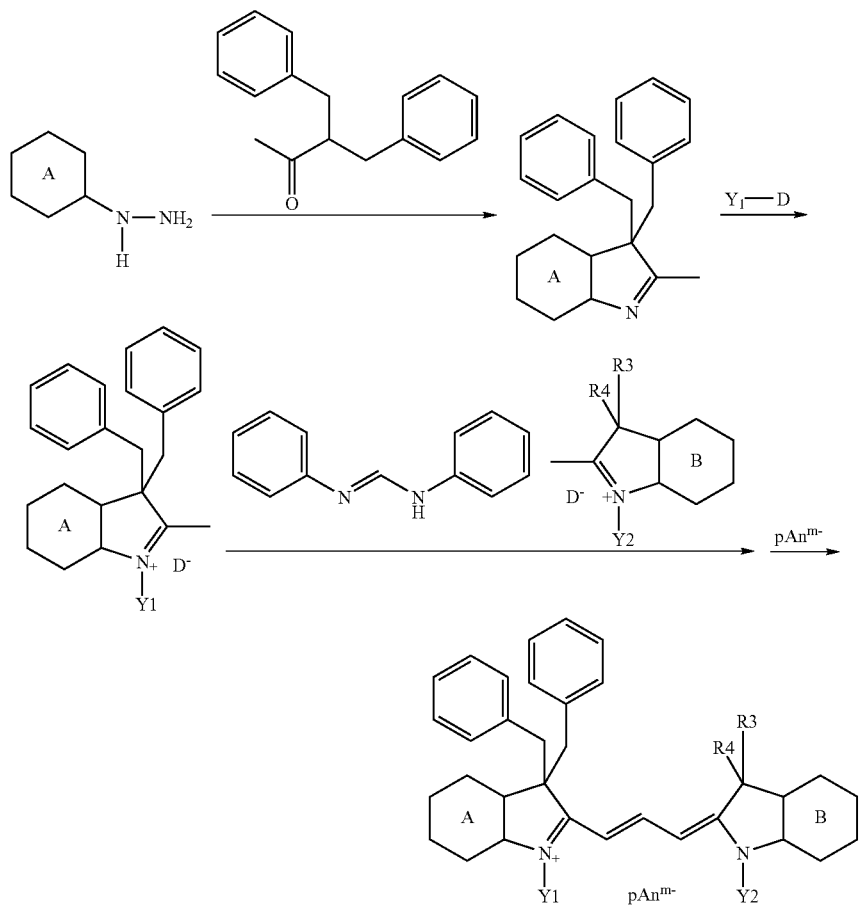

wherein ring A, ring B, R3, R4, Y1, Y2, An$^{m-}$, m, and p are the same definition as general formula (I); and D represent a halogen group, e.g., chlorine, bromine or iodine, or a sulfonyloxy group.

The cyanine compound of the invention functions as an optical element. It is especially suited for use in an optical recording layer of an optical recording medium. The optical recording layer containing the cyanine compound of the invention is formed on a substrate as a thin film by using an optical recording material containing the cyanine compound of the invention. The "optical recording material" according to the present invention includes the cyanine compound of the invention per se and a mixture of the cyanine compound of the invention and an organic solvent and/or other compounds hereinafter described.

While the method of forming the optical recording layer of an optical recording media is not particularly limited, a wet coating technique is generally used, in which a solution of the cyanine compound of the invention, etc. in an organic solvent is applied to a substrate by spin coating, spray coating, dipping or a like method. Suitable organic solvents include lower alcohols, such as methanol and ethanol; ether alcohols, such as methyl cellosolve, ethyl cellosolve, butyl cellosolve, and butyl diglycol; ketones, such as acetone, methyl ethyl ketone, methyl isobutyl ketone, cyclohexanone, and diacetone alcohol; esters, such as ethyl acetate, butyl acetate, and methoxyethyl acetate; acrylic esters, such as ethyl acrylate and butyl acrylate; fluoroalcohols, such as 2,2,3,3-tetrafluoropropanol; hydrocarbons, such as benzene, toluene, and xylene; and chlorinated hydrocarbons, such as methylene dichloride, dichloroethane, and chloroform. The optical recording layer may also be formed by vacuum evaporation, sputtering, and the like.

The thickness of the optical recording layer is usually 0.001 to 10 μM, preferably 0.01 to 5 μm.

The content of the cyanine compound of the invention in the optical recording layer of the optical recording medium is preferably 50% to 100% by weight. The optical recording material of the invention preferably contains 50% to 100% by weight of the cyanine compound of the invention on a solid basis to give the above-recited cyanine compound content in the optical recording layer.

If desired, the optical recording layer can contain compounds commonly employed in an optical recording layer, such as cyanine compounds other than those of the invention, azo compounds, phthalocyanine compounds, and porphin compounds. The optical recording layer can further contain resins, such as polyethylene, polyester, polystyrene, and polycarbonate, surface active agents, antistatic agents, lubricants, flame retardants, radical scavengers (e.g., hindered amines), pit formation accelerators s (e.g., ferrocene derivatives), dispersants, antioxidants, crosslinking agents, light resistance imparting agents, and so forth. The optical recording layer can furthermore contain an aromatic nitroso compound, an aluminum compound, an iminium compound, a bisiminium compound, a transition metal chelate compound, and the like as a quencher for singlet oxygen, etc. These various components are preferably used in the optical recording layer in an amount of up to 50% by weight. Accordingly, the content of these components in the optical recording material of the invention is preferably up to 50% by weight on a solid basis.

Materials of the substrate on which the optical recording layer is provided is not particularly limited as long as it is substantially transparent to writing (recording) light and reading (reproducing) light and include resins, such as polymethyl methacrylate, polyethylene terephthalate, and polycarbonate, and glass. The substrate can have an arbitrary form, including a tape, a drum, a belt, and a disk.

A reflective layer of gold, silver, aluminum, copper, etc. may be formed on the optical recording layer by vacuum evaporation or sputtering. A protective layer of an acrylic resin, an ultraviolet cured resin, etc. may be provided on the optical recording layer.

The optical recording material of the present invention is suitable for optical recording media using a semiconductor laser for writing and reading, especially high-speed recording type optical disks such as DVD-Rs.

EXAMPLES

The present invention will now be illustrated in greater detail with reference to Preparation Examples, Evaluation Example, Examples, and Comparative Examples, but it should be understood that the invention is not construed as being limited thereto.

Preparation Example 1

Preparation of Hexafluorophosphate of Compound No. 10

(a) Synthesis of Indole Derivative

In a reaction flask were put 158.2 g of naphthylhydrazine, 286.0 g of 1,1-dibenzylacetone, and 542 g of ethanol and stirred at 70° C. for 1 hour. To the mixture was added dropwise 125 g of a 35 wt % hydrochloric acid aqueous solution at 70° C., followed by allowing the mixture to react at 80° C. for 1 hour. After cooling to room temperature, 200 g of toluene was added, and the reaction mixture was washed with three 300 g portions of water and dried over anhydrous sodium sulfate. The resulting solution was freed of the solvent, and the residue was purified by silica gel chromatography to give 40.0 g (yield: 11.1%) of an indole derivative having benzyl groups as brown liquid.

(b) Synthesis of Intermediate Compound

In a reaction flask were put 18.7 g of the indole derivative prepared in (a) above, 12.8 g of 1-propane iodide, and 39.9 g of propanol and allowed to react at 100° C. for 12 hours. The reaction system was freed of the solvent, and the residue was dissolved in 5.4 g of ethanol while hot. To the solution was added 27 g of butyl acetate for crystallization. The crystals were collected by filtration and dried in vacuo at 80° C. for 2 hours to afford 4.9 g of an intermediate compound in a yield of 18.4% as yellow crystals.

(c) Synthesis of Cyanine Compound

Into a reaction flask were charged 2.71 g of the intermediate compound prepared in (b) above, 2.47 g of an intermediate compound A shown below, 1.56 g of acetic anhydride, and 8.05 g of pyridine, and the mixture was allowed to react at 60° C. for 4 hours. To the reaction mixture was added 30 g of chloroform, followed by washing with 30 g of water. A solution of 4.2 g of potassium hexafluorophosphate in 20 g of water was added thereto, followed by stirring at room temperature for 30 minutes. The aqueous phase was removed. A solution of 2.8 g of potassium hexafluorophosphate in 15 g of water was added to the organic phase, followed by stirring at room temperature for 30 minutes. The aqueous phase was removed. A solution of 1.4 g of potassium hexafluorophosphate in 15 g of water was additionally added, followed by stirring at room temperature for 30 minutes. The aqueous phase was removed. The resulting organic phase was washed with three 15 g portions of water, dried over anhydrous sodium sulfate, and freed of the solvent to give an oily product. The oily product was heated, and 40 g of methanol was added thereto dropwise while refluxing. The reaction system was cooled to 25° C., and the precipitated crystals were collected by filtration, washed with methanol and dried in vacuo at 120° C. for 2 hours to furnish 2.5 g (yield: 64.6%) of purple crystals. The resulting crystals were analyzed to give the following results and identified to be a hexafluorophosphate of compound No. 10.

Intermediate Compound A:

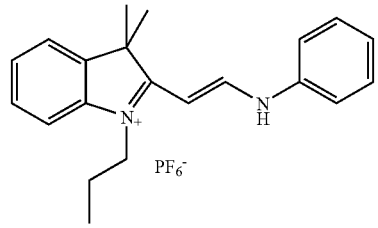

Results of Analyses:

Optical characteristics ($2.326 \times 10^{-6}$ mol/l in chloroform):

$\lambda_{max}$: 589 nm; $\epsilon$: $1.26 \times 10^5$

Melting point (endothermic peak temperature in DSC in nitrogen; rate of temperature rise: 10° C./min): 249° C.

Molecular weight (TOF-mass spectrometry): 760.9

$^1$H-NMR (DMSO) spectrum: shown in FIGS. 1-*a* and 1-*b*

Preparation Example 2

Preparation of Hexafluorophosphate of Compound No. 12

(d) Synthesis of Intermediate Compound

In an autoclave were put 18.7 g of the indole derivative prepared in Preparation Example 1, 10.7 g of methyl iodide, and 38 g of methanol and allowed to react at 100° C. for 12 hours. The reaction system was freed of the solvent, and the residue was dissolved in 5.0 g of ethanol while hot. To the solution was added 50 g of butyl acetate for crystallization. The crystals were collected by filtration and dried in vacuo at 80° C. for 2 hours to give 5.5 g of an intermediate compound in a yield of 21.9% as yellow crystals.

(e) Synthesis of Cyanine Compound

Into a reaction flask were charged 2.52 g of the intermediate compound prepared in (d) above, 2.49 g of intermediate compound B shown below, 1.53 g of acetic anhydride, and 7.91 g of pyridine, and the mixture was allowed to react at 50° C. for 4 hours. To the reaction mixture were added 16 g of chloroform and a solution of 1.65 g of potassium hexafluorophosphate in 20 g of water, followed by stirring at room temperature for 30 minutes. The aqueous phase was removed. A solution of 0.7 g of potassium hexafluorophosphate in 15 g of water was added to the organic phase, followed by stirring at room temperature for 30 minutes. The aqueous phase was removed. A solution of 0.7 g of potassium hexafluorophosphate in 15 g of water was additionally added, followed by stirring at room temperature for 30 minutes. The aqueous phase was removed. The resulting organic phase was washed with three 15 g portions of water, dried over anhydrous sodium sulfate, and freed of the solvent to give an oily product. The oily product was heated, and 15 g of methanol was added thereto dropwise while refluxing. The reaction system was cooled to 25° C., and the precipitated crystals were collected by filtration, washed with methanol and dried in vacuo at 120° C. for 2 hours to furnish 1.2 g (yield: 31.8%) of purple crystals. The resulting crystals were analyzed to give the following results and identified to be a hexafluorophosphate of compound No. 12.

Intermediate Compound B:

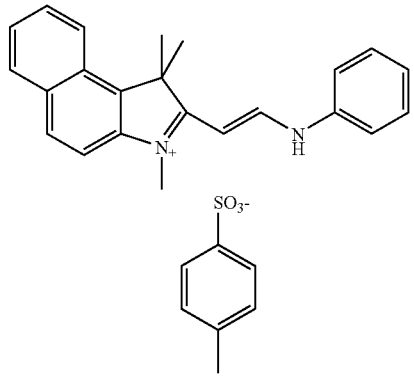

Results of Analyses:

Optical characteristics (3.418×10$^{-6}$ mol/l in chloroform):

$\lambda_{max}$: 607 nm; $\epsilon$: 1.19×10$^5$

Melting point (endothermic peak temperature in DSC in nitrogen; rate of temperature rise: 10° C./min): 231° C.

Molecular weight (TOF-mass spectrometry): 754.8

$^1$H-NMR (CDCl$_3$) spectrum: shown in FIGS. 2-a, 2-b, and 2-c.

Preparation Example 3

Preparation of Hexafluorophosphate of Compound No. 19

(f) Synthesis of Intermediate Compound

In a reaction flask were put 16.2 g of a starting material of formula shown below that was obtained by condensation of N-methyl-N-(4-chlorophenyl)hydrazine and 4-phenylbutan-2-one, 13.4 g of benzyl bromide, and 26.5 g of ethanol and allowed to react at 75° C. for 14 hours. To the reaction mixture was added 60 g of ethyl acetate, followed by refluxing for 30 minutes. The crystals thus formed were collected by filtration, washed with ethyl acetate, and dried in vacuo at 80° C. for 2 hours to give 19.0 g of an intermediate compound in a yield of 71.8% as white crystals.

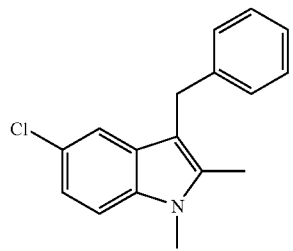

(g) Synthesis of Cyanine Compound

Into a reaction flask were charged 6.92 g of the intermediate compound prepared in (f) above, 1.54 g of N,N'-diphenylamine, 2.40 g of acetic anhydride, and 12.42 g of pyridine, and the mixture was allowed to react at 78° C. for 4 hours. To the reaction mixture were added 25 g of chloroform and a solution of 4.33 g of potassium hexafluorophosphate in 50 g of water, followed by stirring at room temperature for 30 minutes. The aqueous phase was removed. A solution of 2.10 g of potassium hexafluorophosphate in 25 g of water was added to the organic phase, followed by stirring at room temperature for 30 minutes. The aqueous phase was removed. A solution of 1.1 g of potassium hexafluorophosphate in 25 g of water was additionally added, followed by stirring at room temperature for 30 minutes. The aqueous phase was removed. The resulting organic phase was washed with three 30 g portions of water, dried over anhydrous sodium sulfate, and freed of the solvent to give an oily product. The oily product was heated, and 14 g of methanol was added thereto dropwise while refluxing. The reaction system was cooled to 25° C., and the precipitated crystals were collected by filtration, washed with methanol and dried in vacuo at 120° C. for 2 hours to furnish 2.2 g (yield: 32.1%) of green crystals. The resulting crystals were analyzed to give the following results and identified to be a hexafluorophosphate of compound No. 19.

Results of Analyses:

Optical characteristics (3.820×10$^{-6}$ mol/l in chloroform):

$\lambda_{max}$: 585 nm; $\epsilon$: 1.56×10$^5$

Melting point (endothermic peak temperature in DSC in nitrogen; rate of temperature rise: 10° C./min): 244° C.

Molecular weight (TOF-mass spectrometry): 875.8

$^1$H-NMR (DMSO) spectrum: shown in FIGS. 3-a, 3-b, and 3-c.

Evaluation Example

The cyanine compounds obtained in Preparation Examples 1 to 3 and comparative compounds 1 to 3 shown below were subjected to differential thermal analysis (DTA) to determine the thermal decomposition temperature (the exothermic peak temperature) in temperature rise at 10° C./min in nitrogen. The results obtained are shown in Table 1 below.

TABLE 1

Comparative Compound 1:

Comparative Compound 2:

Comparative Compound 3:

| | Cation Moiety | Anion Moiety | Thermal Decomposition Temperature (° C.) |
|---|---|---|---|
| Prepn. Ex. 1 | Compound No. 10 | $PF_6^-$ | 247.9 |
| Prepn. Ex. 2 | Compound No. 12 | $PF_6^-$ | 233.5 |
| Prepn. Ex. 3 | compound No. 19 | $PF_6^-$ | 245.5 |
| | Comp. Compound 1 | $PF_6^-$ | 282.5 |
| | Comp. Compound 2 | $PF_6^-$ | 292.0 |
| | Comp. Compound 3 | $PF_6^-$ | 300.0 |

It was confirmed by the results in Table 1 that the cyanine compounds according to the present invention have a low thermal decomposition temperature. This proves the cyanine compounds of the invention to be suitable as an optical recording material fit for high-speed recording.

Examples 1 to 3

Preparation of Optical Recording Media and Evaluation:

A titanium chelate compound T-50 (available from Nippon Soda Co., Ltd.) was applied to a polycarbonate disk substrate having a diameter of 12 cm, followed by hydrolysis to form an undercoating layer having a thickness of 0.01 µm. A 2 wt % solution of each of the cyanine compounds obtained in Preparation Examples 1 to 3 in 2,2,3,3-tetrafluoropropanol was applied onto the undercoating layer by spin coating to form an optical recording layer having a thickness of 100 nm. The transmitted UV spectrum and the reflected UV spectrum (incidence angle: 5°) of the thus prepared optical recording medium were measured. The results obtained are shown in Table 2.

A transmitted light spectrum is related to writing performance of an optical recording medium. The absorption intensity at $\lambda_{max}$ of a given optical recording medium being taken as 1, if the relative intensity is smaller than 0.15, the medium has poor writing performance. If it exceeds 0.50, the optical recording layer exhibits low light resistance and poor archival stability. Accordingly, the absorption intensity at a writing wavelength is properly in the range between 0.15 and 0.50. A reflected light spectrum is related to reproducing performance of an optical recording medium. In a reproduce mode, a read laser beam is reflected on a medium, and the record is detected as a difference in reflected light quantity at the laser wavelength. Accordingly, a recording medium having a maximum reflection wavelength nearer to the read laser beam wavelength is more desirable.

TABLE 2

| Example No. | Cyanine Compound | Trans-mitted Light $\lambda_{max}$ (nm) | Transmitted Light (Relative Intensity) | Reflected Light $\lambda_{max}$ (nm) |
|---|---|---|---|---|
| 1 | Compound No. 10 $PF_6^-$ salt (Prepn. Ex. 1) | 604 | 635 nm (0.202) | 625 |
| 2 | Compound No. 12 $PF_6^-$ salt (Prepn. Ex. 2) | 618.5 | 650 nm (0.289) 660 nm (0.182) | 646 |
| 3 | Compound No. 19 $PF_6^-$ salt (Prepn. Ex. 3) | 595 | 620 nm (0.373) 635 nm (0.161) | 621 |

The results in Table 2 reveal that the optical recording medium having an optical recording layer formed on a substrate using the cyanine compound of the present invention is suited to write and read with a laser beam having a wavelength of 620 nm, 635 nm, 650 nm or 660 nm, the standards of DVD-Rs.

INDUSTRIAL APPLICABILITY

The present invention provides a novel cyanine compound suited to optical recording applications, an optical recording material containing the same, and an optical recording medium containing the same.

The invention claimed is:

1. An optical recording medium comprising a substrate and a cyanine compound selected from the group consisting of the following:

Compound No. 1

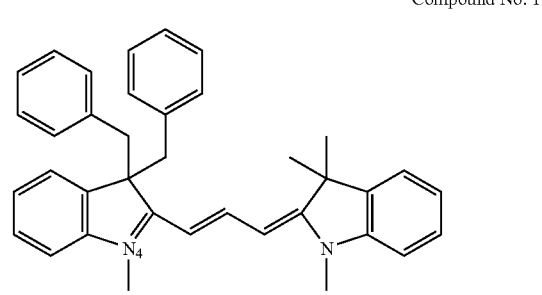

-continued
Compound No. 2
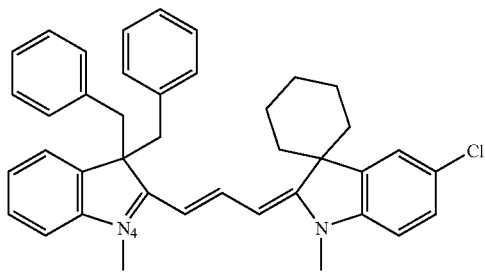
Compound No. 3
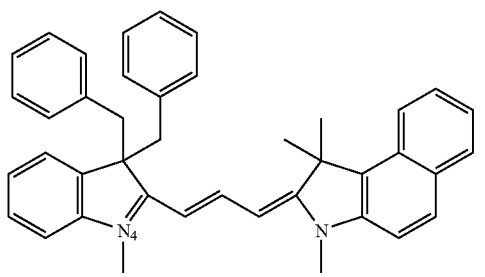
Compound No. 4
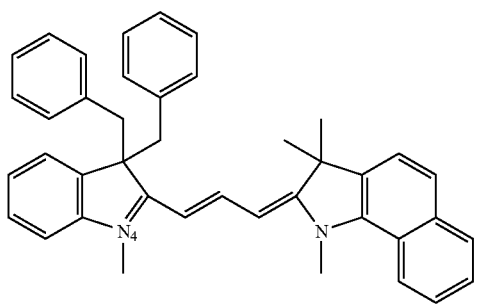
Compound No. 5
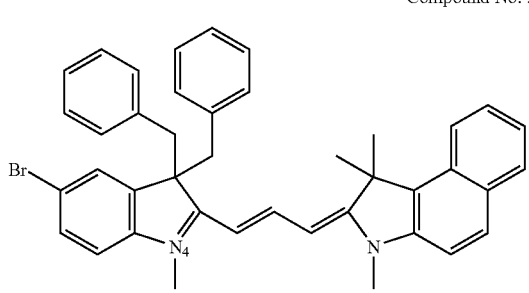
Compound No. 6
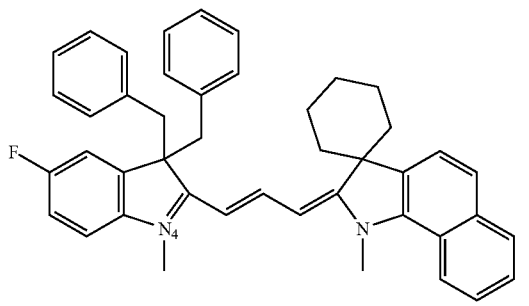
-continued
Compound No. 7
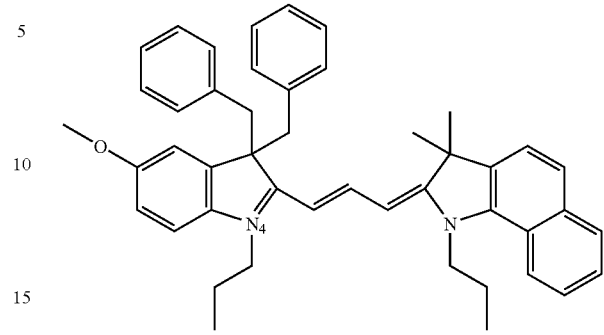
Compound No. 8
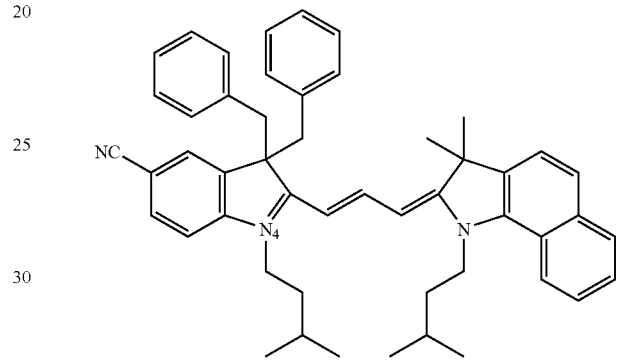
Compound No. 9
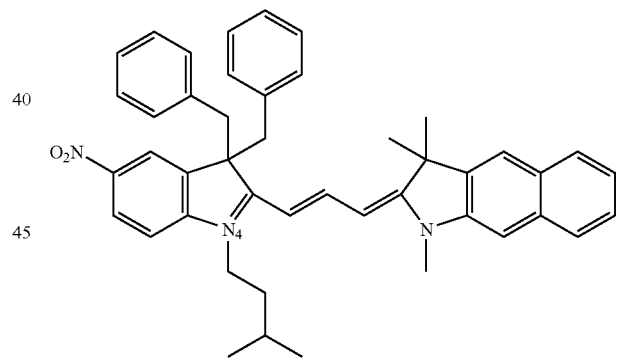
Compound No. 10
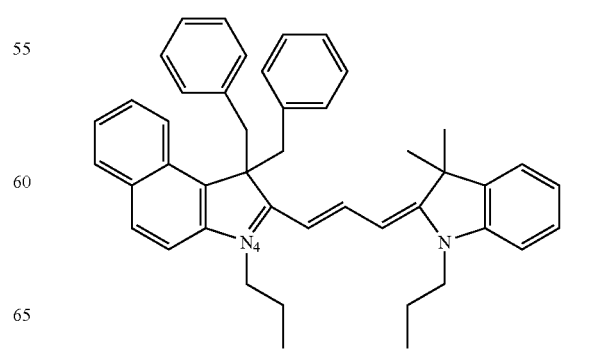

Compound No. 11
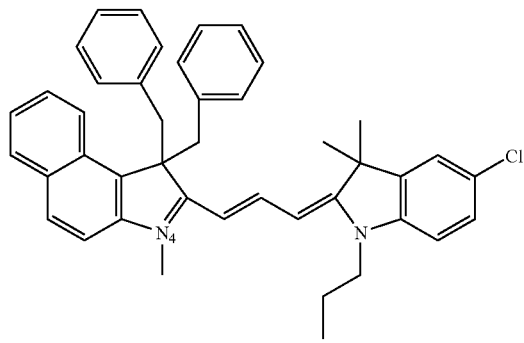
Compound No. 15
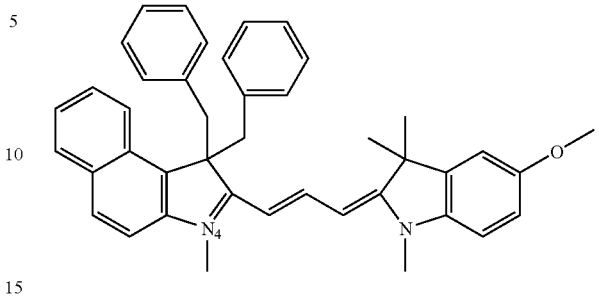
Compound No. 12
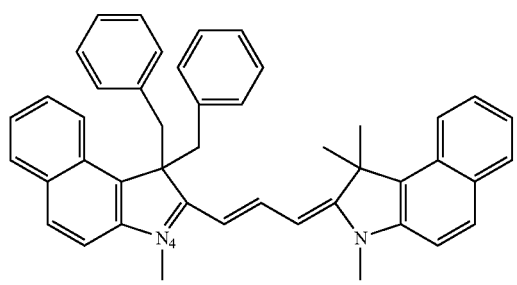
Compound No. 16
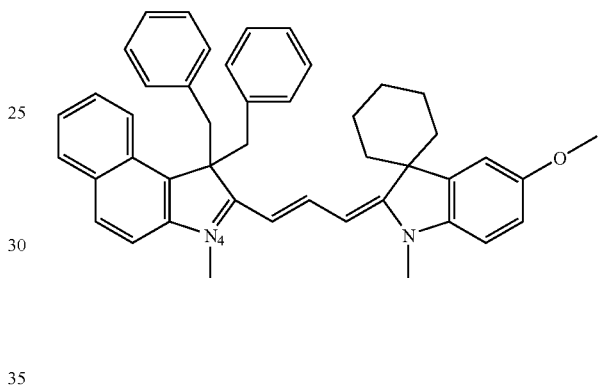
Compound No. 13
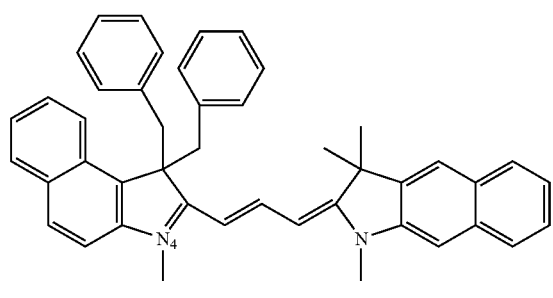
Compound No. 17
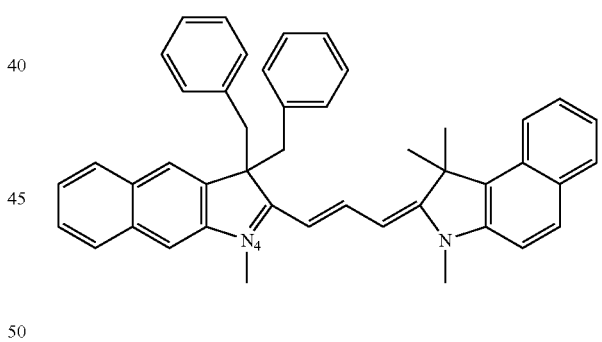
Compound No. 14
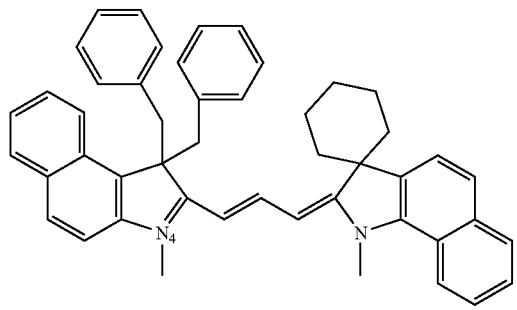
Compound No. 18
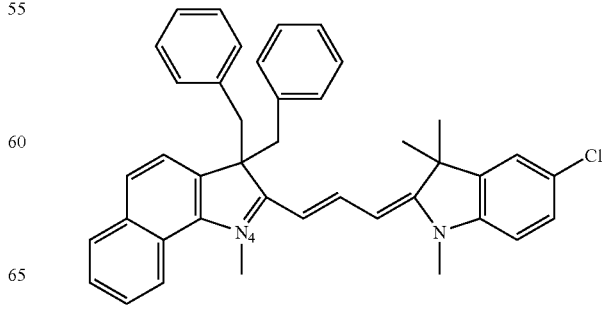

-continued
Compound No. 20
Compound No. 23
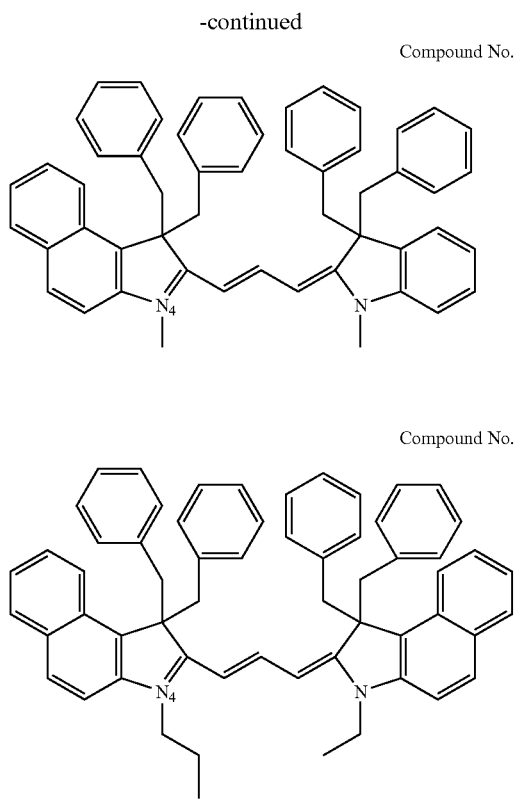
-continued
Compound No. 24
Compound No. 25
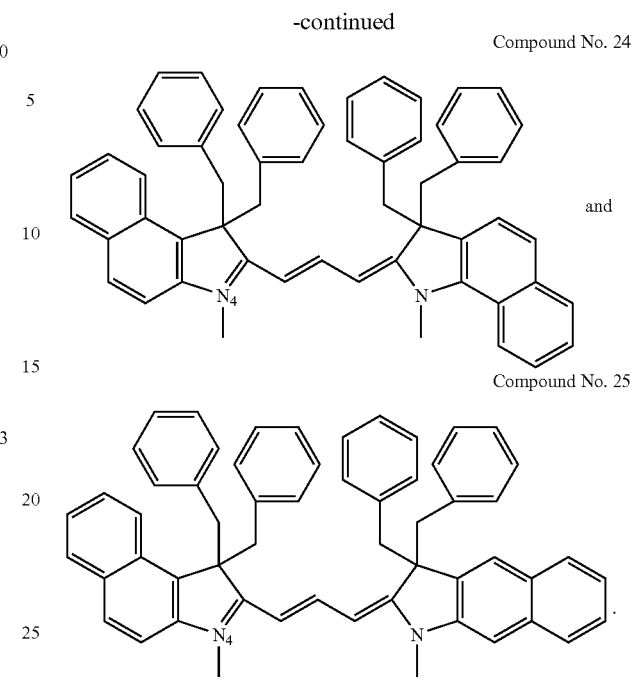
and wherein the cyanine dye has a decomposition temperature of less then 247.9° C.
2. An optical recording medium comprising a thin film of the optical recording material of claim 1 on the substrate.
* * * * *